US00PP36068P2

(12) United States Plant Patent
Jan Kraan

(10) Patent No.: US PP36,068 P2
(45) Date of Patent: Aug. 13, 2024

(54) ***HYDRANGEA PLANT* NAMED 'BOKOMAPISHAD'**

(50) Latin Name: *Hydrangea paniculata*
Varietal Denomination: Bokomapishad

(71) Applicant: Kees Jan Kraan, Alphen aan den Rijn (NL)

(72) Inventor: Kees Jan Kraan, Alphen aan den Rijn (NL)

(73) Assignees: BOOT & CO BOOMKWEKERIJEN BV, Boskoop (NL), PART INTEREST; KOLSTER BV, Boskoop (NL), PART INTEREST ( * ) Notice: Subject to any disclaimer, the term of this patent is extended or adjusted under 35 U.S.C. 154(b) by 0 days.

(21) Appl. No.: 18/504,655

(22) Filed: Nov. 8, 2023

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea paniculata* plant named 'Bokomapishad' that is characterized by its compact plant shape, its strong and healthy foliage including while in bloom, its sterile flowers that are white in color and mature to a deep pink color, its ovate to conical shaped inflorescences with obtuse tips, and its inflorescences that consist of both fertile and sterile flowers with the fertile flowers mostly hidden by sterile flowers.

2 Drawing Sheets

Botanical classification: *Hydrangea paniculata.*
Varietal denomination: 'Bokomapishad'.

BACKGROUND OF THE INVENTION

The present invention relates to a new and distinct cultivar of *Hydrangea paniculata* and will be referred to hereafter by its cultivar name, 'Bokomapishad'. 'Bokomapishad' represents a new panicle *Hydrangea*, a perennial shrub grown for use as a landscape plant.

'Bokomapishad' was derived from an ongoing breeding program conducted by the Inventor in Boskoop, The Netherlands. The goals of the breeding program are to develop new cultivars of *Hydrangea paniculata* with compact and dense plant habits and dense paniculate inflorescences with unique shapes and colors.

'Bokomapishad' originated as a seedling that arose from seed planted from open pollination of *Hydrangea paniculata* 'Phantom' (not patented) in July of 2011. The male parent is therefore unknown. 'Bokomapishad' was selected as a single unique plant in August of 2020 from the resulting seedlings.

Asexual propagation of the new cultivar was first accomplished by softwood stem cuttings by the Inventor in Boskoop, The Netherlands in August of 2016. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bokomapishad' as a unique cultivar of *Hydrangea.*

1. 'Bokomapishad' exhibits a compact plant shape.
2. 'Bokomapishad' exhibits strong and healthy foliage including while in bloom.
3. 'Bokomapishad' exhibits sterile flowers that are white in color and mature to a deep pink color.
4. 'Bokomapishad' exhibits ovate to conical shaped inflorescences with obtuse tips.
5. 'Bokomapishad' exhibits inflorescences that consist of both fertile and sterile flowers with the fertile flowers mostly hidden by sterile flowers.

The parent plant of 'Bokomapishad' differs from 'Bokomapishad' in having a taller plant height, inflorescences that are broader in size with an apiculate shaped tip, and sterile flowers that change color later after maturing with a less intense and lighter pink color. 'Bokomapishad' can be most closely compared to the *Hydrangea paniculata* cultivars 'Jane' (U.S. Plant Pat. No. 22,330) and 'Limelight' (U.S. Plant Pat. No. 12,874). 'Jane' is similar to 'Bokomapishad' in plant shape and inflorescence shape. 'Jane' differs from 'Bokomapishad' in having a more compact plant habit, inflorescences that are broadly ovate in shape, and sterile flowers that are green-white in color and change color later after maturing with a less intense and lighter pink color. 'Limelight' is similar to 'Bokomapishad' in overall plant shape. 'Limelight' differs from 'Bokomapishad' in having a taller plant height, inflorescences that are broadly ovate in shape, and sterile flowers that are green-white to lime green in color and change color later after maturing with a less intense and lighter pink color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plant Development Services, Mark Watch Plants, Sunset Plant Collection, youlin-sad, and compumir.

BRIEF DESCRIPTION OF THE DRAWINGS

The accompanying color photographs illustrate the overall appearance and distinct characteristics of the new *Hydrangea*. The photograph was taken of a two-year-old plant of 'Bokomapishad' as grown in 3-gallon containers in Loxley, Alabama.

The photograph in FIG. 1 provides a view of 'Bokomapishad' in late summer.

Figure 1:
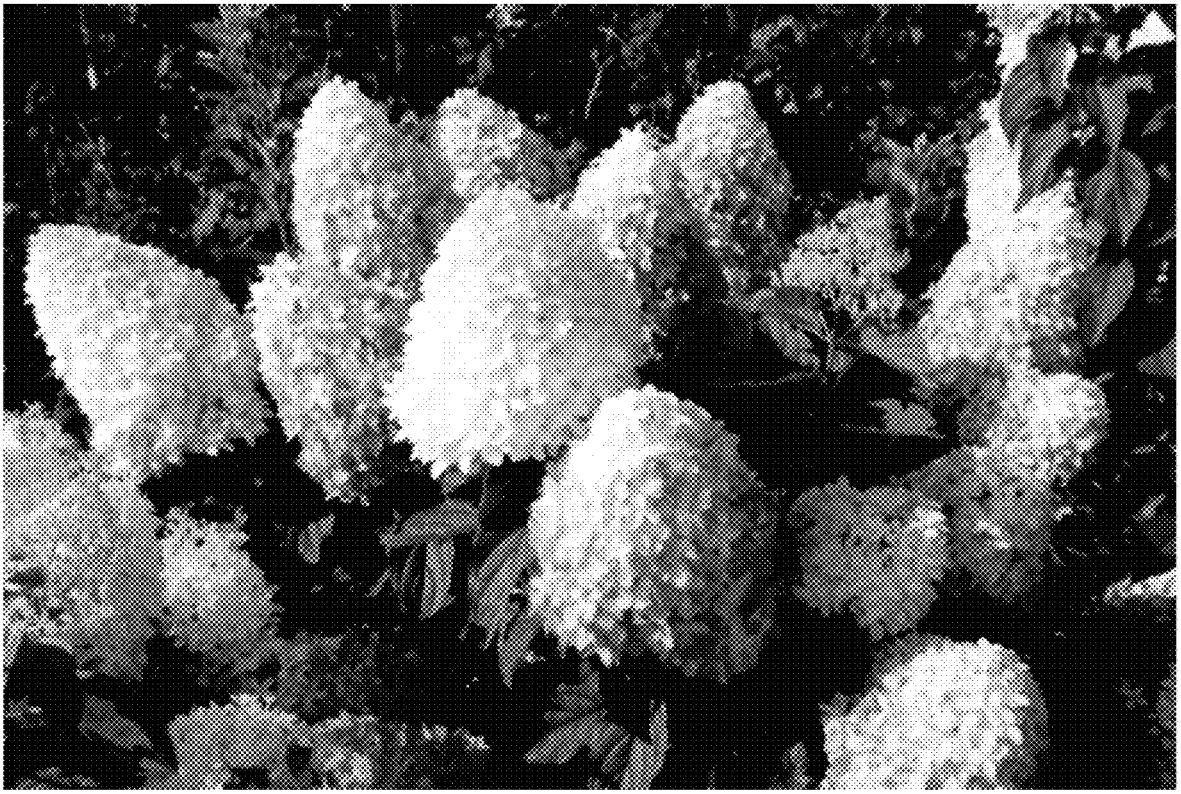
Figure 2:
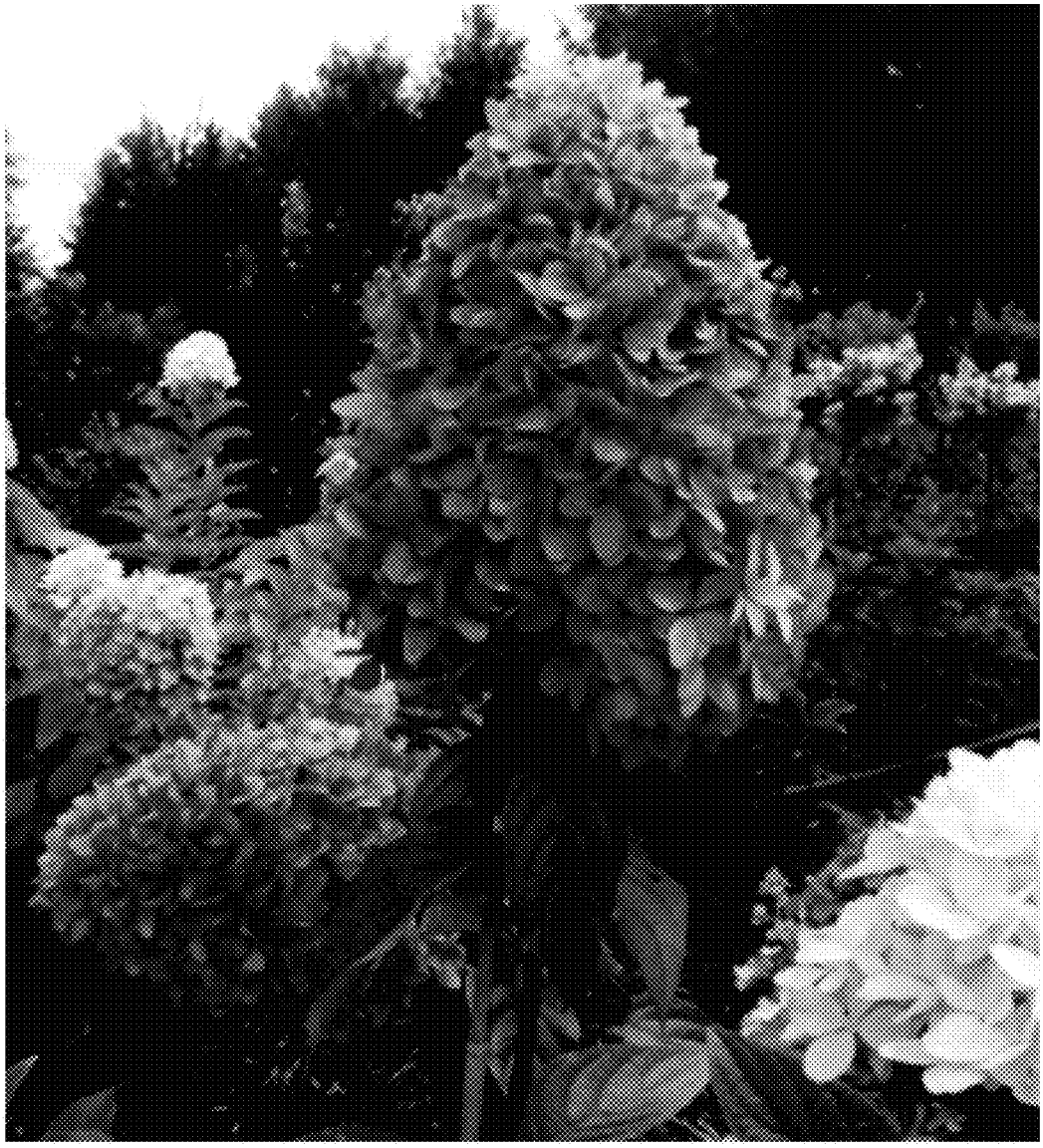

The photograph in FIG. 2 provides a close-up view of an inflorescence of 'Bokomapishad' in fall.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of two-year-old plants of 'Bokomapishad' as grown in 3-gallon containers in Loxley, Alabama. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—6 weeks from mid-summer to early fall in The Netherlands.

*Plant type*.—Deciduous shrub, panicle type *Hydrangea*.

*Plant habit*.—Compact, upright.

*Height and spread*.—Reaches 95 cm in height and 70 cm in width as a 2-year-old plant in a container, matures in the landscape to 1.5 m in height and 1 m in width.

*Hardiness*.—At least in U.S.D.A. Zones 5 to 9.

*Diseases and pests*.—No susceptibility and resistance to diseases or pests has been observed.

*Root description*.—Fine, fibrous and dense, 161A in color.

*Propagation*.—Softwood stem cuttings.

*Root development*.—An average of 3 weeks for root initiation with a young rooted plant produced in an average of 12 weeks (in summer).

*Growth rate and vigor*.—Moderate.

Branch description:

*Branch shape*.—Round.

*Branch strength*.—Very strong.

*Branch color*.—Young; 138C and 145D, mature and older branches; 200B, base striations of 200B and 191A, trunk 199B.

*Branch size*.—Main (trunk); average of 5 cm in length and 2 cm in diameter, lateral; 82 cm, 5 mm in diameter.

*Branch surface*.—Young; matte, velvety, moderately covered with round to linear shaped lenticels, an average of 2 mm in diameter, 145D in color, mature; slightly glossy, sheen, smooth and moderately covered with round to linear shaped lenticels, an average of 2 mm in diameter, 161B in color, older wood and trunk; rugose, a blend of glossy and matte, base of truck slightly exfoliating.

*Branch aspect*.—Upright.

*Internode length*.—An average of 5.5 cm.

*Branching*.—Main; 1, lateral; 4.

Foliage description:

*Leaf shape*.—Ovate.

*Leaf arrangement*.—Opposite.

*Leaf division*.—Simple.

*Leaf base*.—Acute.

*Leaf apex*.—Apiculate.

*Leaf margins*.—Serrate.

*Leaf blade lobing*.—Shallow.

*Leaf venation*.—Pinnate, color; upper surface N144B, lower surface 142D.

*Leaf size*.—An average of 14 cm in length and 7 cm in width.

*Leaf attachment*.—Petiolate.

*Leaf number*.—An average of 12 (6 pairs) per lateral stem.

*Leaf surface*.—Both surfaces slightly glossy and glabrous.

*Leaf color*.—Young and mature upper surface 147A, young and mature lower surface; a blend of 144A and 144B.

*Petioles*.—An average of 3 cm in length and 3 mm in width, rounded with a concave line on the top, both surfaces glossy, densely covered with minute pubescent hairs that match surface colors, color; upper surface 144B, lower surface 142D.

Inflorescence description:

*Inflorescence type*.—Terminal conical panicle, comprised of single sterile flowers and fertile flowers, fertile flowers.

*Lastingness of inflorescence*.—Sterile flowers; persistent for an average of 6 weeks, fertile flowers; self-cleaning, an average of 5 days.

*Inflorescence number*.—One per lateral stem.

*Inflorescence size*.—An average of 22 cm in height and 20 cm in diameter.

*Flower number*.—An average of 400 sterile flowers and 50 fertile flowers per panicle.

*Flower fragrance*.—None.

*Flower aspect*.—Sterile and fertile flowers; upright to outward.

*Flower size*.—Sterile flowers; (including showy sepals) up to 4 cm in diameter and 1 cm in depth, fertile flowers; an average of 6 mm in diameter and 3 mm in depth.

*Flower type*.—Rotate.

*Peduncles*.—Primary peduncles; moderately strong, bendable, flattened oval in shape, an average of 2 cm in length and 2 mm in width, secondary peduncles 1 cm in length and 1 mm in width, 142B in color, becomes flushed with 52C in late summer, peduncle surfaces densely covered with short, soft tangled floccose pubescence matching surface color.

*Pedicels*.—Sterile flowers; moderate strength, an average of 2 cm in length and 2 mm in width, 157C in color, becomes flushed with 52C in late summer, surface is matte and glabrous, fertile flowers; almost sessile, an average of 1 mm in length and width, 142D in color, becomes flushed with 52C in late summer, surface is matte and glabrous.

*Petals*.—Sterile flowers: flower bud; 2 mm in depth and diameter, round in shape, young; 157C in color, mature and in autumn; 54A, when petals open; 4 to 5, rotate, concave in shape, acute apex, cuneate base, entire margins, 2 mm in length and 1 mm in width, both surfaces are glabrous, satiny, and matte, color; both surfaces when opening and fully open NN155C, petals drop after opening later in the season, fertile flowers: flower bud; 3 mm in depth and diameter, round in shape, color; 157C, flushed with 142A, when petals open; 5, rotate, concave in shape, acute apex, cuneate base, entire margins, 3 mm in length, 1 mm in width, both surfaces are glabrous, satiny, and matte, color; both surfaces when opening and fully open NN155C, petals drop after opening later in the season.

*Sepals*.—Sterile flowers; varies between 4 to 6 per flower, rotate, obovate to linear in shape, apex is obcordate to rounded, base is cuneate, entire margins, 2.5 cm in length, 1.5 cm in width, both surfaces glabrous, satiny, and matte, color: when opening upper and lower surface; 149B to 149A, fully open upper and lower surface; NN155A and NN155D, late summer sepals start becoming flushed around the margins with 56A, outer edges 186A, sepals in early autumn; young 155A, mature a blend of 56D, 54A, 155A, fading to a blend of 145A and 56A, fertile flowers; average of 5, fused, 10% of top portion free, acute apex, broadly cuneate base, entire margins, 0.9 mm in length and width, surfaces are matte and glabrous, young both surfaces; 142C in color, mature and fading both surfaces; 142A and 54A.

Reproductive organs:

*Gynoecium*.—Sterile flowers; 1 pistil, stigma and style; pointed and non-distinguishable, 1 mm in length, 157A in color, ovary; non-distinguishable, fertile flowers; 1 pistil, 3-forked, stigma; club-shaped and 142C in color, style; 0.4 mm in length, 142C in color, ovary is superior, 1 mm in depth and diameter, 142C in color.

*Androecium*.—Sterile flowers; an average of 8 stamens, filaments; an average of 1 mm in length, 0.5 mm in diameter, NN155C in color, anthers; round in shape, an average of 0.5 mm in diameter, NN155C in color, fading to 200A in color, pollen; low, NN155C in color, fertile flowers; an average of 7 stamens, filaments; an average of 1.5 mm in length, 0.5 mm in diameter, NN155C in color, anthers; oval in shape, an average of 0.8 mm in diameter, 200A in color, pollen; none observed.

*Fruit and seed*.—None observed to date.

It is claimed:

1. A new and distinct cultivar of *Hydrangea* plant named 'Bokomapishad' substantially as herein illustrated and described.

* * * * *